United States Patent

Tamura et al.

[11] Patent Number: 5,378,244
[45] Date of Patent: Jan. 3, 1995

[54] 2-ALKOXY-3,5-DIAMINOPYRIDINE DERIVATIVES AND THEIR SALTS, AND DYE COMPOSITIONS FOR KERATINOUS FIBERS CONTAINING THE DERIVATIVES OR SALTS

[75] Inventors: Tadashi Tamura, Oyama; Akira Kiyomine, Ichikai; Osamu Morita, Kaminokawa; Michio Tanaka, Takanezawa; Masahiko Ogawa, Omiya; Hidetoshi Tagami, Chiba; Toru Yoshihara, Ichikawa, all of Japan

[73] Assignee: KAO Corporation, Tokyo, Japan

[21] Appl. No.: 26,284

[22] Filed: Mar. 4, 1993

[30] Foreign Application Priority Data

Mar. 6, 1992 [JP] Japan .................. 4-049575

[51] Int. Cl.⁶ .................. A61K 7/13; C07D 213/63
[52] U.S. Cl. .................. 8/409; 8/405; 8/406; 8/408; 8/410; 8/423; 8/568; 546/261; 546/264
[58] Field of Search .................. 8/423, 416, 421, 408, 8/409, 405, 406, 410, 568; 546/255, 261, 264

[56] References Cited

U.S. PATENT DOCUMENTS 4,473,375 9/1984 Clausen .................. 8/409

FOREIGN PATENT DOCUMENTS 0441263 8/1991 European Pat. Off.
1397551 4/1964 France.

OTHER PUBLICATIONS

Chemical Abstracts, vol. 60, No. 7, Mar. 30, 1964, AN-7987d-g, J. Barycki, et al., "Preparation of 2-Alkoxy-3,5-Diaminopyridines".

Primary Examiner—Paul Lieberman
Assistant Examiner—Caroline L. Dusheck
Attorney, Agent, or Firm—Oblon, Spivak, McClelland, Maier, & Neustadt

[57] ABSTRACT

A dye composition for keratinous fibers which contains a coupler and a developer are disclosed. The present coupler component is a novel 2-alkoxy-3,5-diaminopyridine derivatives of the formula (1):

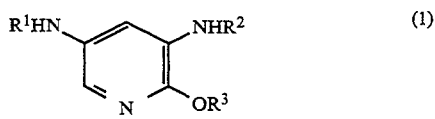

wherein R1 and R2 are the same or different from each other and independently represent a hydrogen atom, a lower alkanoyl group or a lower alkyl group which may be substituted by at least one hydroxyl group, and R3 is a lower alkyl group which may be substituted by at least one hydroxyl group, or a salt thereof; provided that R1 and R2 are not both a hydrogen atom or an acetyl group at the same time. The present 2-alkoxy-3,5-diaminopyridine derivatives are useful as couplers in dye compositions, and are capable of dyeing keratinous fibers such as hair in a bright blue color with excellent dyeability. Dye compositions containing the present compounds as a coupler show excellent resistance to discoloration, excellent resistance to shampooing and excellent resistance to friction.

11 Claims, No Drawings

2-ALKOXY-3,5-DIAMINOPYRIDINE DERIVATIVES AND THEIR SALTS, AND DYE COMPOSITIONS FOR KERATINOUS FIBERS CONTAINING THE DERIVATIVES OR SALTS

BACKGROUND OF THE INVENTION i) Field of the Invention

The present invention relates to novel 2-alkoxy-3,5-diaminopyridine derivatives and their salts, and dye compositions for keratinous fibers which contain the derivatives or salts as a coupler. The present dye compositions impart a bright blue tone with enhanced fastness to keratinous fibers.

ii) Discussion of the Background

Conventionally, keratinous fibers (such as hair) have generally been dyed by so-called oxidation dye compositions, which contain developers and couplers in combination. The dyeing mechanism of the oxidation dyes is primarily based on a chemical oxidation reaction, where a coupling agent is oxidized, and simultaneously, the oxidative coupling of a developer and a coupler firmly dyes the keratinous fiber.

Conventional developers include p-phenylene diamine derivatives, p-aminophenol derivatives, diaminopyridine derivatives, 4-aminopyrazolone derivatives and heterocyclic hydrazone. Conventional couplers include alpha-naphthol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, hydroquinone, 2,4-diaminoanisole, m-toluylenediamine, o-aminophenol, resorcin, resorcin monomethyl ether, m-phenylene diamine, 1-phenyl-3-methyl-5-pyrazolone, 1-phenyl-3-amino-5-pyrazolone, 1-phenyl-3,5-diketopyrazolidine, 1-methyl-7-dimethylamino-4-hydroquinolone-2,1-amino-3-acetylacetamino-4-nitrobenzol, 1-amino-3-cyanacetylamino-4-nitrobenzol, m-aminophenol, 4-chlororesorcin, 2-methylresorcin, 2,4-diaminophenoxy ethanol, 2,6-diaminopyridine, 3,5-diaminotrifluoromethylbenzene, 2,4-diaminofluorobenzene, 3,5-diaminofluorobenzene, 2,4-diamino-6-hydroxypyrimidine, 2,4,6-triaminopyrimidine, 2-amino-4,6-dihydroxypyrimidine, 4-amino-2,6-dihydroxypyrimidine and 4,6-diamino-2-hydroxypyrimidine.

Conventional couplers to be incorporated in oxidation dye compositions, however, have provided only insufficient results in terms of color brightness, dyeability and color fastness. Since these properties are greatly influenced by the chemical characteristics of the coupler, it is very important to search for a coupler capable of achieving improved dye properties.

Among the conventional oxidation dye compositions, m-phenylene diamine and 2,6-diaminopyridine provide a blue tone of high brightness. However, the blue tone obtained is easily discolored, the color is quickly washed away by shampooing, and in addition, the color fastness is poor.

SUMMARY OF THE INVENTION

Accordingly, an object of the present invention is to provide a coupler component which imparts a blue tone of high brightness and an enhanced color fastness to keratinous fibers.

Another object of the invention is to provide a novel 2-alkoxy-3,5-diaminopyridine derivative of the formula (1):

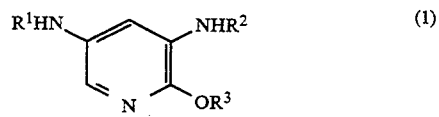

wherein R1 and R2 independently represent a hydrogen atom, a lower alkanoyl group or a lower alkyl group which may be substituted by at least one hydroxyl group, and R3 is a lower alkyl group which may be substituted by at least one hydroxyl group, or a salt thereof; provided that both R1 and R2 are not simultaneously a hydrogen atom or an acetyl group.

A further object of the present invention is to provide a dye composition for keratinous fibers which comprises a developer component and a coupler component, wherein the coupler component comprises a compound of the formula (1) as described above or a salt thereof.

A still further object of the present invention is to provide a method of dyeing keratinous fibers using the compound of the formula (1) as described above or a salt thereof as a coupler.

DETAILED DESCRIPTION OF THE PREFERRED EMBODIMENTS

The present inventors have synthesized many compounds, have investigated their characteristics as a coupler, and have found that novel 2-alkoxy-3,5-diaminopyridine derivatives of the formula (1) and their salts provide dye compositions with excellent dyeability and color fastness, and are very useful as a coupler component in an oxidation dye composition.

The present 2-alkoxy-3,5-diaminopyridine derivatives are represented by the aforementioned formula (1), wherein R1 and R2 are the same or different from each other and independently represent a hydrogen atom, a lower alkanoyl group or a lower alkyl group which may be substituted by at least one hydroxyl group, and R3 is a lower alkyl group which may be substituted by at least one hydroxyl group, provided that both R1 and R2 are not simultaneously a hydrogen atom or an acetyl group.

The lower alkanoyl group of R1 or R2 may be a linear or branched alkanoyl group having 2 to 5 carbon atoms. Examples of suitable lower alkanoyl groups include a formyl group, an acetyl group, a propionyl group, a butyryl group, a valeryl group and an isovaleryl group. The lower alkyl group of R1, R2 or R3 may be a linear or branched alkyl group having from 1 to 5 carbon atoms, such as a methyl group, an ethyl group, a propyl group, an isopropyl group, an n-butyl group, an isobutyl group, an sec-butyl group and an amyl group. These lower alkyl groups may be substituted by 1 or more, preferably from 1 to 3 hydroxyl groups.

The 2-alkoxy-3,5-diaminopyridine derivatives (1) are prepared, for example, by the following reaction scheme:

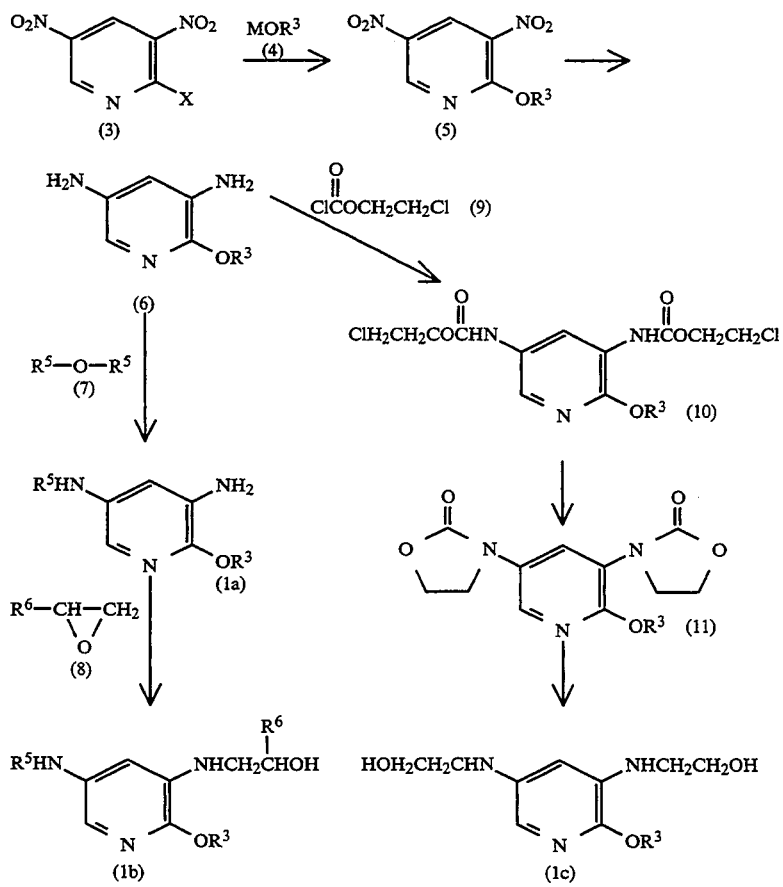

wherein R3 is as defined above, X is a halogen atom, M is an alkali metal atom, R5 is a lower alkanoyl group and R6 is a lower alkyl group of from 1 to 3 carbon atoms, which may be substituted with 1 or 2 hydroxyl groups.

In other words, 2-halogeno-3,5-dinitropyridine (3) is reacted with a metal alkoxide (4) to obtain compound (5), which is then reduced to obtain compound (6). Compound (6) and an acid anhydride (7) are reacted to produce compound (1a), which is further reacted with an alkylene oxide (8) to obtain compound (1b).

If compound (6) is diacylated with beta-chloroethyl chloroformate (9), compound (10) is obtained. Compound (10) is cyclized to form compound (11), then hydrolyzed as a whole to obtain compound (1c).

Examples of the starting material, 2-halogeno-3,5-dinitropyridine (3), include 2-chloro-3,5-dinitropyridine, 2-bromo-3,5-dinitropyridine, 2-fluoro-3,5-dinitropyridine and 2-iodo-3,5-dinitropyridine, 2-chloro-3,5-dinitropyridine being preferred.

Examples of metal alkoxide (4) include sodium alkoxides, potassium alkoxides and lithium alkoxides, with sodium alkoxides being preferred. The metal alkoxide is produced from the reaction between either sodium hydride or sodium metal and an alcohol, including monohydric alcohols such as methanol, ethanol, propanol, isopropanol, butanol, pentanol, hexanol and isomers thereof, and polyhydric alcohols such as ethylene glycol, diethylene glycol, triethylene glycol, tetraethylene glycol, propylene glycol, dipropylene glycol, butylene glycol and glycerol.

The reaction between compound (3) and compound (4) proceeds in a solvent such as the above-mentioned alcohol, toluene or xylene, with stirring for a length of time from 5 minutes to 5 hours at a temperature of from $-5°$ C. to the boiling point of the solvent. The obtained compound (5) is catalytically hydrogenated in a conventional manner applicable for reducing a nitro group, for example, in a hydrogen atmosphere or in the presence of a known hydrogen source (such as cyclohexadiene), using a catalyst such as palladium on carbon. Preferably, the reaction is performed in an autoclave.

The reaction between compound (6) and acid anhydride (7) is preferably carried out in a solvent which is miscible with water, such as methanol or ethanol, while controlling the pH of the solution in the range of from 6 to 7. The reaction between compound (1a) and alkylene oxide (8) is preferably carried out at a temperature of from 20° to 100° C., preferably in an autoclave.

The acylation of compound (6) is carried out under conventional conditions for an acylation reaction; for example, by heating to a temperature of from 30° C. to the boiling point of the solvent in the presence of a base. The cyclization and hydrolysis are carried out by heating in the presence of a base such as calcium hydroxide and/or potassium hydroxide. The cyclization and hydrolysis may be performed in the same reaction mixture without isolating the cyclized intermediate (11).

in order to isolate the present compound (1) from the reaction mixture, conventional recrystallization processes and/or column chromatography can be applied.

The thus obtained 2-alkoxy-3,5-diaminopyridine derivatives (1) can be used in the form of a corresponding salt, which is easier to handle and which improves the preparation of target products containing or using the same. Examples of preferable salts include salts obtained from the reaction of the 2-alkoxy-3,5-diaminopyridine with inorganic or organic acids such as hydrochloric acid, sulfuric acid, phosphoric acid, acetic acid, propionic acid, lactic acid and citric acid.

The present dye composition for keratinous fibers comprises a developer component and the aforementioned compound (1) or a salt thereof as a coupler component. Developers useful as a component of the present dye composition are not particularly limited, as long as they can be employed in a conventional oxidation dye composition. Suitable developers include p-phenylenediamine, toluene-2,5-diamine, N-phenyl-p-phenylenediamine, p-aminophenol, methoxy-p-phenylenediamine, 2,5-diaminopyridine, p-methylaminophenol, tetraminopyrimidine, 2,4-diaminophenol, o-aminophenol, o-chloro-p-phenylenediamine, 4,4′-diaminodiphenylamine, N-(2-hydroxyethyl)-p-phenylene diamine and N,N-bis-(2-hydroxyethyl)-p-phenylenediamine. Among them, especially preferred for obtaining a blue tone color of high brightness and enhanced fastness are the p-phenylenediamine derivatives of the following formula (2):

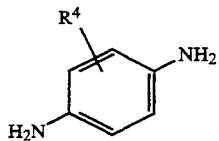
(2)

wherein $R_4$ is a hydrogen atom, chlorine atom or a methyl group.

The amounts of the developer and of the coupler of the formula (1) in the present dye composition can be such that one is in excess relative to the other, but it is preferred that the molar ratio of developer to coupler fall in the range of from 1:0.5 to 1:2.

Developers and couplers are used singly or in combination, respectively. If necessary for obtaining a desired color tone, additional conventional couplers and/or direct dyes can be incorporated into the present dye composition. It is preferred to incorporate a developer and a coupler, each in amounts of from 0,001 to 10% by weight of the composition (hereinafter may be simply referred to as %), preferably from 0.01 to 5%.

The present dye composition for keratinous fibers undergoes an oxidation coupling reaction in the presence of oxygen in the atmosphere. Such an oxidation coupling reaction results in keratinous fibers such as the hair and the like being dyed. It is, however, preferred to induce an oxidation coupling reaction by the addition of oxidation-inducing chemicals. Preferred examples of the oxidation-inducing chemicals include hydrogen peroxide; hydrogen peroxide adducts of urea, melamine or sodium borate; and a mixture of such hydrogen peroxide adducts and potassium peroxide-2 sulfate.

The present dye composition for keratinous fibers may further contain optional ingredients which are useful in the manufacture of cosmetics, as along as they do not impede the effects of the present invention. Examples of such optional ingredients include humectants (emulsifiers) such as alkyl benzenesulfonates, aliphatic alcohol sulfates, alkylsulfonates, aliphatic alkanolamides and ethylene oxide adducts of aliphatic alcohols; viscosity modifiers such as methylcellulose, starch, higher aliphatic alcohols, paraffin oils and aliphatic acids; reducing agents such as sulfites; stabilizers such as hydroquinone derivatives and chelating agents; oils such as silicones, higher alcohols and various nonionic surfactants; texture modifiers such as cationic polymers; bases for hair styling compositions; solubilizers; and perfumes. If humectants are incorporated, the amount thereof is preferably from 0.5 to 30 wt. % of the total weight of the composition, and if viscosity modifiers are incorporated, the amount thereof is preferably from 0.1 to 25 wt. % of the total weight of the composition.

The present dye composition for keratinous fibers is prepared by blending the above-described essential components and optional components in a conventional blending process. The present dye composition can take any physical form, but preferred physical forms include creams, emulsions, gels and solutions, preferably having a pH of from 6 to 11.

To dye keratinous fibers, the present dye composition is first mixed with an oxidation-inducing chemical as described above to provide a dye liquid where oxidation coupling takes place. Then, the obtained dye liquid is applied to keratinous fibers by a conventional process. The dye liquid is contacted with dye fibers for a length of time of from 5 to 50 minutes, preferably for 25 to 30 minutes. The dyed fibers are then washed and dried. Here, the dye liquid is preferably applied to the fibers at a temperature of from 15° to 40° C.

The present dye composition for keratinous fibers provides a blue tone of high brightness and enhanced dyeability and fastness. In other words, the present composition is resistant to discoloration or fading as a result of washing (shampooing), and/or friction.

Other features of the present invention will become apparent in the course of the following descriptions of exemplary embodiments, which are given for illustration of the invention, and are not intended to be limiting thereof.

EXAMPLES

The present invention will now be described by way of examples, which however, should not be construed as limiting the invention thereto.

Referential Example 1.

A 14% methanol solution of sodium methoxide was added to 25.0 g (120 mmol) of 2-chloro-3,5-dinitropyridine, and the mixture was stirred for 15 minutes at room temperature. The mixture was added to 200 ml of a saturated aqueous ammonium chloride solution, and extracted with 200 ml of ethyl acetate. Washing with saturated saline, drying over anhydrous sodium sulfate, filtering and distilling under reduced pressure (bath temp. 40°–60° C., 40–20 mmHg) yielded yellow crystals, which were recrystallized from methanol to obtain 19.5 g (91.8 mmol) of 2-methoxy-3,5-dinitropyridine as pale yellow crystals (yield: 80%).

Referential Example 2.

75 ml of toluene was added to 7.5 g of sodium hydride (60% in oil), and the mixture was cooled to 0° C., and 70 ml of ethylene glycol was added thereto over the course of 30 minutes. To the obtained solution was added 25.0 g (120 mmol) of 2-chloro-3,5-dinitropyridine, the temperature was raised to room temperature, and the mixture was stirred for 15 minutes. The resulting solution was added to 200 ml of a saturated aqueous ammonium chloride solution, and the resulting mixture was extracted with 200 ml of ethyl acetate. Washing the ethyl acetate extract with saturated saline, drying over anhydrous sodium sulfate, filtering and distilling under reduced pressure (bath temp. 40°–60° C., 40°–20mmHg) yielded yellow crystals, which were recrystallized from ethanol to obtain 23.2g (101 mmol) of 2-(3,5-dinitro-2-pyridyloxy)ethanol as pale yellow crystals (yield: 82%).

Example 1.

Synthesis of 3-amino-5-acetamide-2-methoxypyridine:

4 g (20 mmol) of 2-methoxy-3,5-dinitropyridine was dissolved in 200 ml of degassified ethanol. A catalyst (180 mg of 5% palladium on carbon) was added thereto and the mixture was stirred in a hydrogen atmosphere of 30 atm hydrogen pressure in an autoclave at room temperature for 2 hours. The reaction mixture was filtered through Celite to remove the catalyst, and subsequently, 40 ml of water was added. While maintaining the temperature at about 10° C., acetic anhydride (14 mmol, 1.4 ml) was added in portions of about 0.1 ml each, along with four drops of an aqueous 48% NaOH solution, at intervals of 10 minutes, maintaining the pH at about 6–7 during the course of the addition.

Stirring was continued for 50 minutes, and the reaction mixture was then diluted with water of 500 ml and extracted with chloroform, then subjected to distillation.

The product obtained was a 9:1 mixture of the corresponding 5-acetamide and 3 acetamide as shown by $^1$H-NMR. After primary purification by silica gel column chromatography (Merck Co., Si60, ethyl acetate), recrystallization from ethyl acetate yielded 1.9 g (10 mmol) of 3-amino-5-acetamido-2-methoxypyridine as a pale green solid (yield: 51% based on the amount of acetic anhydride).

Melting point: 152.1°–154.0° C.

$^1$H-NMR (200 MHz, DMSO-d$_6$) δ ppm; 1.99 (3H, s), 3.80 (3H, s), 5.00 (2H, s), 7.23 (1H, d, J=2.2), 7.50 (1H, d, J=2.2), 9.67 (1H, s)

IR (KBr) ν cm$^{-1}$; 3476, 3364, 3248, 3200, 1668, 1622, 1540, 1484, 1464, 1412, 1370, 1352, 1260, 1024, 518

Elemental analysis (as C$_8$H$_{11}$N$_3$O$_2$) Calculated: C 53.03%, H 6.11%, N 23.19%; Found: C 52.98%. H 6.05%, N 23.01%.

Example 2.

Synthesis of 2-(3-amino-5-acetamide-2-pyridyloxy)ethanol:

8.5 g (37 mmol) of 2-(3,5-dinitro-2-pyridyloxy)ethanol was dissolved in 250 ml of degassified ethanol. The mixture was stirred in the presence of 400 mg of 5% palladium on carbon as a catalyst under 20 atm hydrogen pressure at room temperature for 2 days in an autoclave. The reaction mixture was filtered through Celite to remove the catalyst, and subsequently, 120 ml of ethanol and 74 ml of water were added to the filtrate. The temperature was maintained at about 10° C., and 3.7 ml of acetic anhydride (37 mmol) was added in approximately 0.2 ml portions, along with 5 drops of an aqueous 48% NaOH solution from a Pasteur pipette at intervals of 10 minutes, maintaining the pH at about 6–7. The mixture was stirred for an additional 30 minutes. The mixture was concentrated, then purified by silica gel column chromatography (Merck Co., Si60, ethyl acetate-methanol=10:1). Recrystallization from methanol yielded 4.6 g (22 mmol) of 2-(3-amino-5-acetamido-2-pyridyloxy)ethanol as a green solid (yield: 59%)

Melting point: 145.8° C. (decomposed)

$^1$H-NMR (200 MHz, DMSO-d$_6$) δ ppm; 2.00 (3H, s), 3.2–3.8 (2H, brs.), 3.69 (2H, t, J=4.9 Hz), 4.17 (2H, t, J=4.9 Hz), 4.7–5.5 (1H, brs. ), 7.22 (1H, d, J=1.9 Hz), 7.47 (1H, d, J=1.9 Hz), 9.67 (1H, s)

IR (KBr) ν cm$^{-1}$; 3352, 1662, 1624, 1558, 1456, 1436, 1244, 1046

Elemental analysis (as C$_9$H$_{13}$N$_3$O$_3$) Calculated: C 51.18%, H 6.20%, N 19.89%); Found: C 50.96%, H 6.20%, N 19.87%).

Example 3.

Synthesis of 2-[5-acetamide-3-(2-hydroxyethyl)amino-2-pyridyloxy]ethanol:

4 g (19 mmol) of 2-(3-amino-5-acetamide-2-pyridyloxy)ethanol and 2.5 g (57 mmol) of ethylene oxide were dissolved in 100 ml of ethanol at 0° C. The mixture was then stirred at 80° C. for 4 hours. The product obtained was a mixture of monoalkylated and dialkylated product in a molar ratio of 2:3 (from $^1$H-NMR). After concentration, purification was conducted by silica gel column chromatography (Merck Co., Si60, ethyl acetate-methanol in a gradient of from 20:1 to 5:1) to isolate 2-[5-acetamide-3-(2-hydroxyethyl)amino-2-pyridyloxy]ethanol.

Melting point: 139.0°–140.0 ° C. $^1$H-NMR (200 MHz, DMSO-d$_6$) δ ppm; 2.00 (3H, s), 3.09 (2H, t, J=6.0 Hz), 3.59 (2H, t, J=6.0Hz), 3.70 (2H, t, J=6.0 Hz), 4.21 (2H, t, J=6.0 Hz), 7.04 (1H, d, J=2.3 Hz), 7.56 (1H, d, J=2.3 Hz), 9.73 (1H, s)

IR (KBr) ν cm$^{-1}$; 3394, 3292, 2944, 1653, 1593, 1515, 1446, 1240 Elemental analysis (as C$_{11}$H$_{17}$N$_3$O$_4$) Calculated: C 51.76%, H 6.71%, N 16.46% ); Found: C 51.82%, H 6.69%, N 16.17% ).

Example 4.

Synthesis of 2-[3,5-bis-(2-hydroxyethyl)amino-2pyridyloxy]ethanol:

(i) 37 ml of dioxane was mixed with 4.39 g (26.0 mmol) of 2- (3,5-diamino-2-pyridyloxy)ethanol and 2.93 g (29.3 mmol) of calcium carbonate, and the mixture was heated to 90° C. while nitrogen gas was passed therethrough. To this solution, 8.50 g (59.4 mmol) of beta-chloroethyl chloroformate was added dropwise over the course of 15 minutes, and the resulting mixture was stirred at 90° C. for 30 minutes. After completion of the reaction, the mixture was cooled to 50° C., the insoluble salts were filtered off, and then the filtrate was cooled to room temperature. The filtrate was poured into 250 ml of ice water to allow crystals to precipitate. The crystals were collected by filtration and recrystallized from 150 ml of acetonitrile to obtain 4.86 g (11.2 mmol) of 3,5-bis-[(2-chloroethoxy)carbonylamino]-2-(2-hydroxyethoxy)pyridine as pale red crystals (yield: 43% ).

Melting point: 176.0°–177.5° C. $^1$H-NMR (200 MHz, DMSO-d$_6$) δ ppm; 3.71 (2H, t, J=4.6 Hz), 3.68 (2H, t, J=5.5 Hz), 3.89 (2H, t, J=5.5 Hz), 4.20 (2H, t, J=4.6 Hz), 4.34 (2H, t, J=5.5 Hz), 4.40 (2H, t, J=5.5 Hz), 4.6 (2H, brs.), 7.90 (1H, s), 8.39 (1H, s), 9.0 (1H, brs.)

IR (KBr) ν cm$^{-1}$; 1730, 1705, 1535, 1210, 1088 Elemental analysis (as C$_{13}$H$_{17}$N$_3$O$_6$Cl$_2$ ) Calculated: C 40.85%, H 4.48%, N 10.99%, Cl 18.55%); Found: C 40.48%, H 4.20%, N 10.89% Cl 18.30%).

(ii) 40 ml of an aqueous 5N NaOH solution was added with 4.80 g (11.05 mmol) of 3,5-bis-[(2-chloroethoxy) carbonylamino]-2- (2-hydroxyethoxy)pyridine, and the mixture was heated to reflux for 90 minutes while nitrogen gas was passed therethrough. The reaction mixture was cooled to room temperature, the pH was adjusted to 8 with acetic acid, and the mixture was extracted 12 times with 150 ml of ethyl acetate. The ethyl acetate extracts were combined, washed with a saturated saline solution and dried over anhydrous sodium sulfate. The solvent was distilled off under reduced pressure. The remaining residue was dissolved in 40 ml of methanol, and hydrogen chloride gas was added. 40 ml of ether was added thereto to precipitate crystals. The crystals were filtered and dried to obtain 1.70 g (5.15 mmol) of a double salt of 2-[3,5 -bis-(2 -hydroxyethyl)amino-2-pyridyloxy]ethanol hydrochloride (yield: 47% ).

Melting point: 117.5°–119.0° C. $^1$H-NMR (200 MHz, DMSO-d$_6$) δ ppm; 3.16 (2H, t, J=4.7 Hz), 3.32 (2H, t, J=4.7 Hz), 3.59 (2H, t, J=4.7 Hz), 3.62 (2H, t, J=4.7 Hz), 3.72 (2H, t, J=4.7 Hz), 4.25 (2H, t, J=4.7 Hz), 4.6 (br.), 6.90 (1H, d, J=1.5 Hz), 7.45 (1H, d, J=1.5 Hz)

IR (KBr) ν cm$^{-1}$; 3380, 3220, 1572, 1065 Elemental analysis (as $C_{11}H_{21}N_3O_4Cl_2$) Calculated: C 40.01%, H 6.41%, N 12.73%, Cl 21.47%); Found: C 39.95%, H 6.37%, N 12.79% Cl 21.27%).

Example 5.

100 g of a base composition, formulated as shown below, was blended with 0.005 mol of a developer and 0.005 mol of a coupler, as indicated in Table 1. Subsequently, the pH of the composition was adjusted to 9.5 with ammonia to prepare a dye composition for keratinous fibers. The color tone, resistance to discoloration and resistance to shampooing of the dyed fibers were evaluated. The results are shown in Tables 2 and 3.

| Base composition: | |
| --- | --- |
| Oleic acid | 10 (%) |
| Diethanolamide oleate | 8 |
| Oleyl alcohol | 2 |
| Polyoxyethylene octyldodecylether (average E.O. - 20 mol added) | 10 |
| Ethanol | 15 |
| Propylene glycol | 10 |
| Ammonium chloride | 3 |
| 25% Ammonia | 7 |
| Water | 35 |
| Total | 100 |

Test Method:

100 g of a dye composition for keratinous fibers was mixed with an equal amount by weight of an aqueous 6% hydrogen peroxide solution to prepare a dye liquid. This dye liquid was applied to white hair and allowed to stand for 30 minutes at 30° C. The hair was shampooed with an ordinary shampoo composition and dried. The obtained color of the dyed hair, its resistance to discoloration and its resistance to shampooing were observed. All the tested compositions exhibited good dyeability and brightness of the color.

(1) Resistance to discoloration:

Dyed hair tresses were kept at 40° C., at 75% relative humidity (RH) for 70 hours. Subsequently, they were dried at room temperature. They were visually compared with dyed hair tresses kept at −5° C. (as control samples). The evaluation was based on the following criteria:

A: Almost no discoloration
B: Slight discoloration
C: Significant discoloration (2) Resistance to shampooing:

Dyed hair tresses were shampooed with a neutral shampoo composition in a total of 15 times. They were visually compared with dyed hair tresses which were not shampooed after dyeing, and evaluated based on the following criteria:

A: Almost no color washed off
B: Color slightly washed off
C: Color significantly washed off

TABLE 1

Developer
$P_1$: p-Phenylenediamine
$P_2$: Toluene 2,5-diamine

Coupler
Invention
$C_1$: 3-Amino-5-acetamide-2-methoxypyridine
$C_2$: 2-(3-Amino-5-acetamide-2-pyridyloxy)ethanol
$C_3$: 2-[5-acetamide-3-(2-hydroxyethyl)amino-2-pyridyloxy]ethanol
$C_4$: 2-[3,5-bis-(2-hydroxyethyl)amino-2-pyridyloxyl]ethanol.2HCl Comparison
$C_5$: 2,6-Diaminopyridine
$C_6$: m-Phenylenediamine

TABLE 2

| | Dye compositions for keratinous fibers | | | | | |
| --- | --- | --- | --- | --- | --- | --- |
| | Invention | | | | Comparison | |
| | 1 | 2 | 3 | 4 | 1 | 2 |
| Developer | $P_1$ | $P_1$ | $P_1$ | $P_1$ | $P_1$ | $P_1$ |
| Coupler | $C_1$ | $C_2$ | $C_3$ | $C_4$ | $C_5$ | $C_6$ |
| Color | blue | blue | blue | blue | blue | blue |
| Resistance to Discoloration | A | A | A | A | B | C |
| Resistance to Shampooing | A | A | B | B | C | C |

TABLE 3

| | Dye compositions for keratinous fibers | | | | | |
| --- | --- | --- | --- | --- | --- | --- |
| | Invention | | | | Comparison | |
| | 5 | 6 | 7 | 8 | 3 | 4 |
| Developer | $P_2$ | $P_2$ | $P_2$ | $P_2$ | $P_2$ | $P_2$ |
| Coupler | $C_1$ | $C_2$ | $C_3$ | $C_4$ | $C_5$ | $C_6$ |
| Color | blue | blue | blue | blue | blue | blue |
| Resistance to Discoloration | A | A | A | A | B | C |
| Resistance to Shampooing | A | A | B | B | C | C |

From the results shown in the Tables above, the present dye compositions for keratinous fibers provide excellent resistance to discoloration and excellent resistance to shampooing. Further, the present dye composition exhibit excellent dyeability and brightness of color.

Obviously, numerous modifications and variations of the present invention are possible in light of the above teachings. It is therefore to be understood that within the scope of the appended claims, the present invention may be practiced otherwise than as specifically described herein.

What is claimed is:

1. A 2-alkoxy-3,5-diaminopyridine derivative of the formula (1):

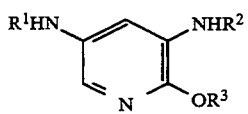 (1)

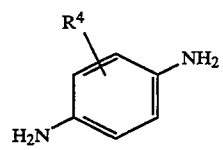 (2)

wherein R1 and R2 independently represent a hydrogen atom, a lower alkanoyl group or a lower alkyl group which is substituted by at least one hydroxyl group, and R3 is a lower alkyl group which may be substituted by at least one hydroxyl group, or a salt thereof; provided that both R1 and R2 are not simultaneously a hydrogen atom or an acetyl group.

2. The 2-alkoxy-3,5-diaminopyridine derivative of claim 1, wherein R1 and R2 independently represent a hydrogen atom, an alkanoyl group having from 2 to 5 carbon atoms, or an alkyl group having from 1 to 5 carbon atoms which is substituted by from 1 to 3 hydroxyl groups, and R3 is an alkyl group having from 1 to 5 carbon atoms which may be substituted by from 1 to 3 hydroxyl groups.

3. A dye composition for keratinous fibers comprising the 2-alkoxy-3,5-diaminopyridine derivative of claim 1 as coupler and a developer.

4. The dye composition of claim 3, wherein said developer is a compound of formula (2):

wherein R4 is a hydrogen atom, a chlorine atom or a methyl group.

5. The dye composition of claim 3, wherein said coupler and said developer are each present in a molar ratio of from 1:0.5 to 1:2.

6. The dye composition of claim 3, wherein said coupler and said developer are each present in an amount of from 0,001 to 10% by weight with respect to the weight of the composition.

7. A method of dyeing keratinous fibers which comprises applying to said keratinous fibers (a) a composition comprising the 2-alkoxy-3,5-diaminopyridine derivative of claim 1 and (b) a developer.

8. The 2-alkoxy-3,5-diaminopyridine derivative of claim 1, 3-amino-5-acetamide-2-methoxypyridine.

9. The 2-alkoxy-3,5-diaminopyridine derivative of claim 1, 2-(3-amino-5-acetamide-2-pyridyloxy)ethanol.

10. The 2-alkoxy-3,5-diaminopyridine derivative of claim 1, 2-[5-acetamide-3-(2-hydroxyethyl)amino-2-pyridyloxy]ethanol.

11. The 2-alkoxy-3,5-diaminopyridine derivative of claim 1, 2-[3,5-bis-(2-hydroxyethyl)-amino-2-pyridyloxy]ethanol.

* * * * *